(12) United States Patent
Weyl et al.

(10) Patent No.: US 6,342,140 B1
(45) Date of Patent: *Jan. 29, 2002

(54) MEASUREMENT DEVICE

(75) Inventors: Helmut Weyl, Schwieberdingen; Bernhard Wild, Markgröningen; Hans-Martin Wiedenmann, Stuttgart, all of (DE)

(73) Assignee: Robert Bosch GmbH, Stuggart (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/091,968

(22) PCT Filed: Aug. 14, 1997

(86) PCT No.: PCT/DE97/01726

§ 371 Date: Nov. 5, 1998

§ 102(e) Date: Nov. 5, 1998

(87) PCT Pub. No.: WO98/19154

PCT Pub. Date: May 7, 1998

(30) Foreign Application Priority Data

Oct. 29, 1996 (DE) .......................................... 196 44 757

(51) Int. Cl.[7] .............................................. G01N 27/407
(52) U.S. Cl. ........................ 204/424; 204/426; 204/428
(58) Field of Search ................................. 204/421–429

(56) References Cited

U.S. PATENT DOCUMENTS

| 4,187,163 | A | * | 2/1980 | Steinke et al. ............... 204/428 |
|---|---|---|---|---|
| 4,216,351 | A | | 8/1980 | Brandeau |
| 4,636,293 | A | * | 1/1987 | Bayha et al. ............... 204/428 |
| 4,830,713 | A | * | 5/1989 | Gagescu ..................... 204/415 |
| 4,923,587 | A | | 5/1990 | Nishio et al. |
| 5,879,527 | A | * | 3/1999 | Kiesele et al. .............. 204/415 |
| 5,900,129 | A | * | 5/1999 | Tsuji et al. .................. 204/428 |
| 6,039,856 | A | * | 3/2000 | Weyl et al. .................. 204/428 |

FOREIGN PATENT DOCUMENTS

| DE | 27 02 578 | 7/1978 |
|---|---|---|
| DE | 28 05 598 | 8/1979 |
| DE | 39 07 549 | 9/1990 |
| DE | 44 39 854 | 5/1996 |
| EP | 0 424 746 | 5/1991 |

* cited by examiner

*Primary Examiner*—T. Tung
(74) *Attorney, Agent, or Firm*—Kenyon & Kenyon (57) ABSTRACT

A measuring device (e.g., an electrochemical sensor) has a sensor element arranged at a measuring point, the sensor element being arranged in a housing, which is linked via electrical connecting lines to an evaluation circuit away from the measuring point, and the electrical connecting lines being routed, at least in the vicinity of the measuring point, in a protective device. Provision is made that the protective device is joined, with a force-locking and form-locking fit, to the housing via an attachment device, which embraces (surrounds) the housing and the protective device, to form a sealing seat.

23 Claims, 5 Drawing Sheets

MEASUREMENT DEVICE

FIELD OF THE INVENTION

The present invention relates to a measuring device, in particular, an electrochemical sensor (e.g., a detecting element).

BACKGROUND INFORMATION

Measuring devices are generally known. For example, electrochemical sensors, formed in a so-called finger type of construction, are installed in motor vehicles for determining the oxygen content in the exhaust gases of internal combustion engines. These measuring devices possess one sensor element which is arranged directly at a measuring point and which is tightly secured in a housing.

The sensor element, as is known, has a solid electrolyte arranged between two electrodes. According to the makeup of the sensor element, an additional heating element is provided. To evaluate the sensor signals detected by the sensor element, or to supply the sensor element with the necessary heating voltage, provision is made for electrical connecting lines, which connect the sensor element to a corresponding circuit arrangement.

Since the sensor element, for example in measuring the oxygen content in exhaust gases, is arranged in an area which is acted upon by a relatively high temperature and in which an increased danger of contamination exists, it is known to shield the electrical connecting lines at least in the vicinity of the measuring device. From German Patent No. DG 2805 598, it is known to run the electrical connecting lines in a protective device designated as a hollow lead. This hollow lead, which is also made of an elastic hose, engages with a shoulder (e.g., a collar) of the measuring device housing and forms a sealing seat with the latter. In this connection, a form-locking fit obtains between the protective device and the housing. The conventional sealing seat has the disadvantage that although sufficient protection is afforded against coarse contamination, e.g., from spray water, nevertheless, fine contamination, such as is caused by a mist-like condensation, as occurs precisely in the mounting location of measuring devices in motor vehicles, is not countered by an adequate sealing effectiveness. The mist-like condensation spreads along the sealing surfaces of the protective device and the housing, which form the sealing seat, and in this way penetrates into the interior of the measuring device.

This protective device also has the disadvantage that it does not provide sufficient protection for the electrical connecting lines against external mechanical damage, for example, by being bent sharply and relatively high temperatures arising at the mounting location of the measuring device.

SUMMARY OF THE INVENTION

The measuring device of the present invention, is advantageous in that it is simple to construct and offers a high level of sealing protection. An absolute sealing tightness of the sealing seat is obtained by the protective device being connected, with a force-locking and form-locking fit, to the housing via a mounting device, which encompasses the housing and the protective device, to form a sealing seat. As a result of the form-locking and force-locking fit between the protective device and the housing, a barrier is established against contact with even mist-like contaminants, so that the spreading contaminants are prevented from passing through the sealing seat.

In an embodiment of the present invention, provision is made that, at least in certain areas in the area of the sealing seat, the housing has a coating, the coating producing a form and force-locking fit between the housing and the protective device, the coating preferably being a PTFE (polytetrafluoroethylene) coating. In this way, a force-locking fit is achieved between the PTFE coating of the housing and the protective device, which is preferably made of a PTFE material, as a result of the hydrophobic properties of the PTFE material. As a result of the water-repelling effect associated therewith, moisture is prevented from penetrating through the sealing seat into the housing.

Due to its high temperature resistance, the PTFE material is additionally suitable for ensuring a permanent sealing effectiveness for the measuring device even under temperature stressing of the housing.

In a further embodiment of the present invention, provision is made that the coating be a PFA (polyfluoroamide) coating. In this way, the property of the material, namely to develop an adhesive effect starting at a certain temperature, is exploited, in that the sealing seat is heated to this required temperature. As a result of the heating, the PFA coating liquefies and produces a form- and force-locking sealing seat between the protective device and the housing. Provision is preferably made to liquefy the PFA coating only partly, through a controlled heating, in particular by an inductive heating, so that the PFA coating remains stable in form and permits a defined production of the sealing seat. In this way, under the given use conditions of the measuring device, a permanent sealing-off of the interior space of the measuring device is assured in a simple manner at the sealing seat between the protective device and the housing.

In another embodiment of the present invention, provision is made that the protective device be an elastic hollow element, whose shell (e.g.,casing), at least in areas, is structurally formed. In this way, it is advantageously achieved that, as a result of the structured surface, the flexibility of the hollow element is maintained, on the one hand, while a mechanical stabilization is achieved, on the other hand, the stabilization preventing a sharp-edged bending of the hollow lead and thus of the electrical connecting lines which are supported in the hollow lead.

In another embodiment of the present invention, provision is made that the elastic hollow element has on its ends attachment segments, which permit the hollow element to be mounted simply and sealingly on the sensor element, on the one hand, and on a contacting device for the electrical connecting lines, on the other hand. The attachment segments are preferably formed so that they can be permanently connected to the corresponding fitting pieces of the sensor element, or to the contacting device, with the aid of a sleeve-like mounting device. In this way, in an advantageous way, surface contact between the elastic hollow element and the sensor element, or the contacting device, is ensured, assuring that the sealing properties will be lasting, even under the influence of temperature or of mechanical strain.

In addition, in another embodiment of the present invention, provision is made that the elastic hollow element be made of a PTFE material. Since, as is well known, this material has high temperature resistance, and the less the material strength, the less the material is subject to temperature-dependent flow, it is thus ensured that an elastic hollow element having the mounting ends is particularly well suited to the oven purpose. In this way, a lasting, sealing connection, capable of withstanding mechanical stresses, can be created particularly at the attachment segment, which is exposed to the sensor element, i.e., to the relatively high temperatures.

Further advantageous embodiments of the invention are disclosed in the other features indicated in the subordinate claims.

DETAILED DESCRIPTION OF THE DRAWINGS

Figure 1:
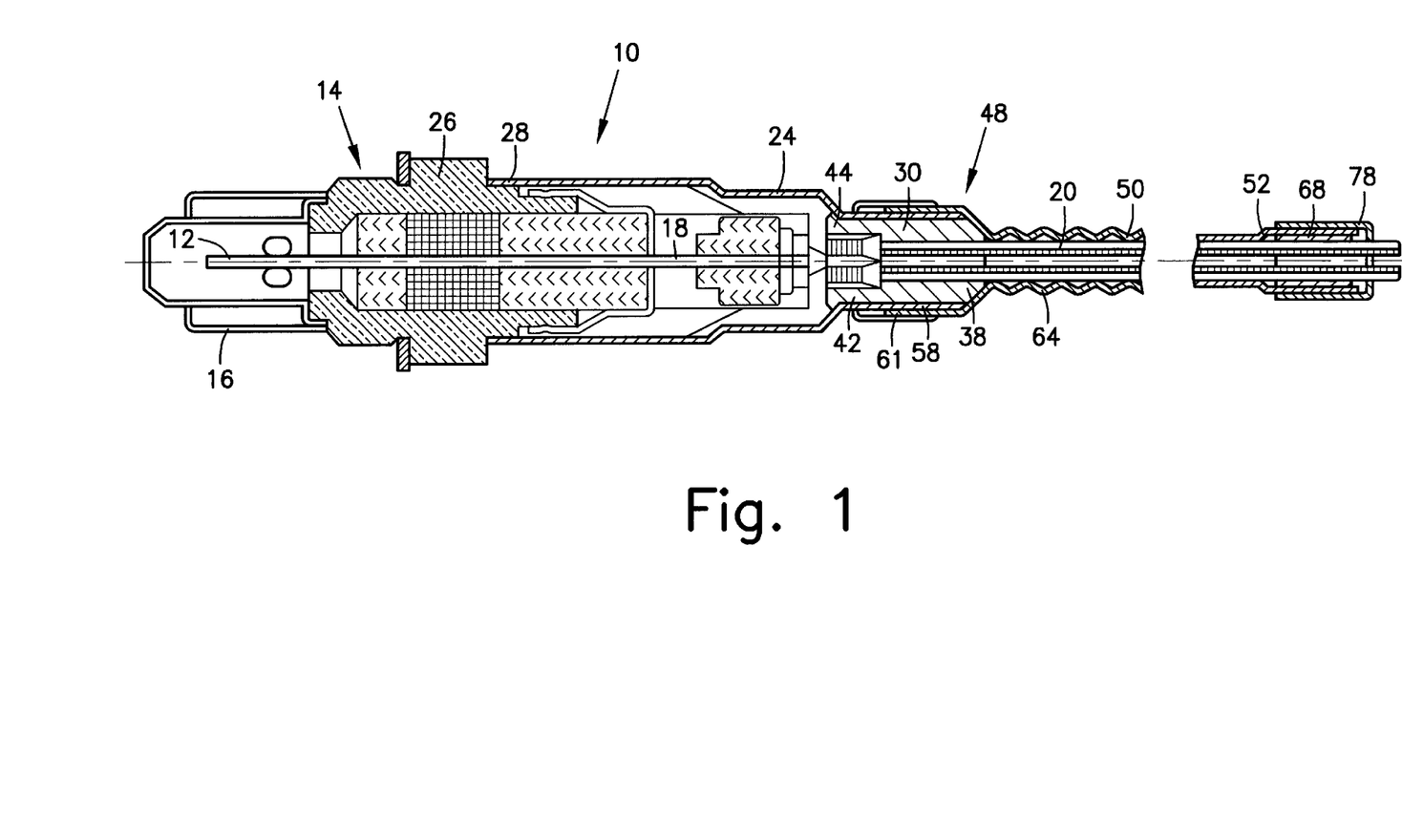
FIG. 1 shows a schematic longitudinal section of a measuring device.

FIG. 1 shows a measuring device 10 in a longitudinal section. Thus, only the components which are essential for the present invention will be explained. The design and the function of measuring device 10 are generally known.

Measuring device 10 has a sensor element 12. Sensor element 12 can, in principle, be any sensor element for measuring a physical quantity. In the example depicted, it is assumed that sensor element 12 is an electrochemical sensor 14, which is used to determine the oxygen content in the exhaust gases of internal combustion engines. Sensor element 12 is arranged in housing 16, which can be secured in an undepicted exhaust pipe. Housing 16 is conveyed through a through hole of the exhaust pipe and is secured by appropriate fastening means, for example, a union nut. Housing 16 is mounted by being sealingly arranged in the through hole.

Housing 16 contains electrodes, which are not shown in FIG. 1 in detail, as well as a heating device 18, by means of which, in a manner not to be elaborated on further below, the oxygen concentration in the exhaust gas of an internal combustion engine can be measured. The electrodes and heating device are connected, via electrical connecting lines 20, to a corresponding evaluation or control circuit. In the depicted example, it is assumed that provision is made for a total of four connecting lines 20. In the case of other, undepicted exemplary embodiments, however, the number of connecting lines can vary in accordance with the make-up of sensor element 12, e.g., the number can be greater or smaller than four.

Connecting lines 20, on the one hand, function to tap off sensor signals and, on the other hand, to make a heating voltage available. In what follows, the support of connecting lines 20 will be explained in greater detail.

Figure 3:
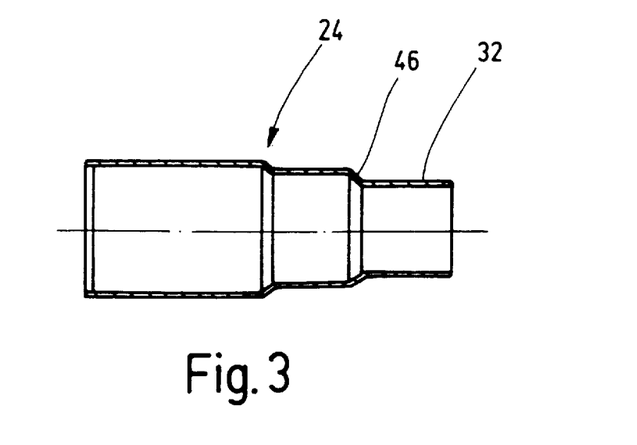
FIG. 3 shows one longitudinal section of a protective sleeve.

At its end away from the measuring point, housing 16 gradually passes over into a protective sleeve 24. Protective sleeve 24 can be formed either in one piece with housing 16, or, as in the depicted example, as a separate part, which is fixedly connected to measuring sensor 14. For this purpose, measuring sensor 14 has a ceramic substructure 26, which has a correspondingly formed shoulder 28. As shown in FIG. 3 in more detail, protective sleeve 24 is configured as a rotationally symmetrical stepped part, i.e., the diameter of protective sleeve 24 decreases by steps over its axial extension. In this way, on the one hand, the mechanical stability of protective sleeve 24 is enhanced and, on the other hand, an input diameter on the side of shoulder 28 can be adjusted to an output diameter, depicted at the right in FIG. 3, leading to a protective device which has yet to be explained.

Figure 7:
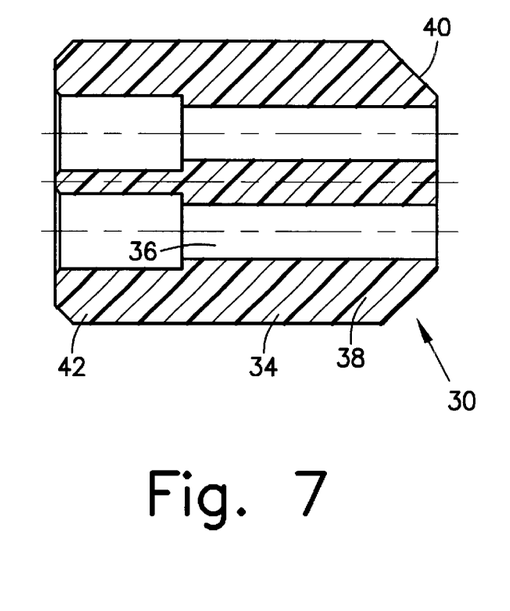
FIG. 7 shows a longitudinal section of a further support sleeve.
Figure 7A:
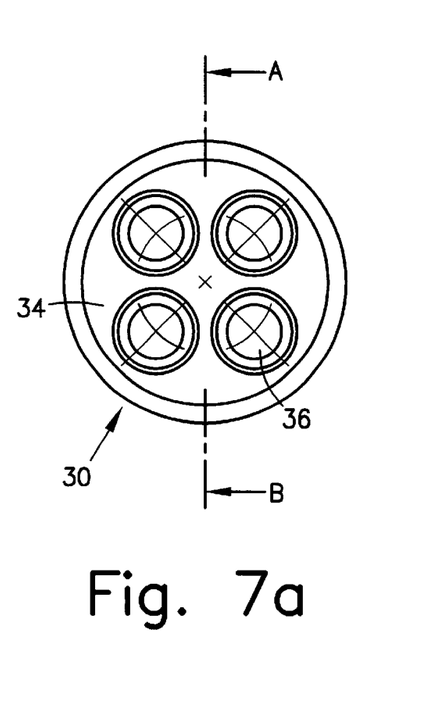
FIG. 7a shows a top view of the further support sleeve.

Protective sleeve 24 has a support sleeve 30, which is arranged within segment 32, which has the smallest diameter (of the steps of protective sleeves 24). Support sleeve 30, which is depicted in greater detail in FIGS. 7 and 7a, has a substructure 34 which is made of a flexible material. Substructure 34 has through holes 36 running in the axial direction which function to accommodate connecting lines 20. Corresponding to the number of connecting lines 20 four through holes 36 are provided in the example depicted. The axial extension of substructure 34 is greater than the axial extension of segment 32 of protective sleeve 24, so that substructure 34 at one end 38 extends beyond protective sleeve 24. End 38 has a conical surface shell area 40. The external diameter of support sleeve 30 is selected so that it can be pressed into segment 32 of protective sleeve 24 without play, and can be fixed because of its elasticity. In this connection, substructure 34 is compressed so that, at its end 42 arranged within protective sleeve 24, a sort of shoulder 44 is produced, which grips a, for example, conical transitional area 46 of protective sleeve 24 from behind, to a segment having a greater diameter. In this way, it is possible to insert support sleeve 30 tightly into protective sleeve 24. Support sleeve 30 is preferably made of a PTFE material. Through holes 36 are preferably constituted such that connecting lines 20 are also sealingly led through them, i.e., no leaks exist between the external casing of connecting lines 20 and through-holes 36. At the same time, support sleeve 30 provides strain relief for connecting lines 20.

End 38 of support sleeve 30 is arranged within a attachment segment 48 of an elastic hollow element 50. Hollow element 50 is depicted in detail in FIG. 2. Hollow element 50 is designed as a molded hose, the latter having at its one end attachment segment 48, at its other end a attachment segment 52, and between attachment segments 48 and 52 a guide segment 54. Attachment segment 48 has an inner diameter which permits it to slide onto segment 32 of protective sleeve 24. In this connection, the axial length of attachment segment 48 is selected such that when attachment segment 48 has been slid onto segment 32, it overlaps entire segment 32, and a conical transition area 56, between attachment segment 48 and guide segment 54, abuts against surface shell 40 of support sleeve 30, which is similarly conical. As a result of this design of support sleeve 30, attachment segment 48, segment 32, and support (protective) sleeve 24, a sealing surface is created over a large surface area, which prevents impurities from penetrating into protective sleeve 24 and thus into housing 16.

Figure 6:
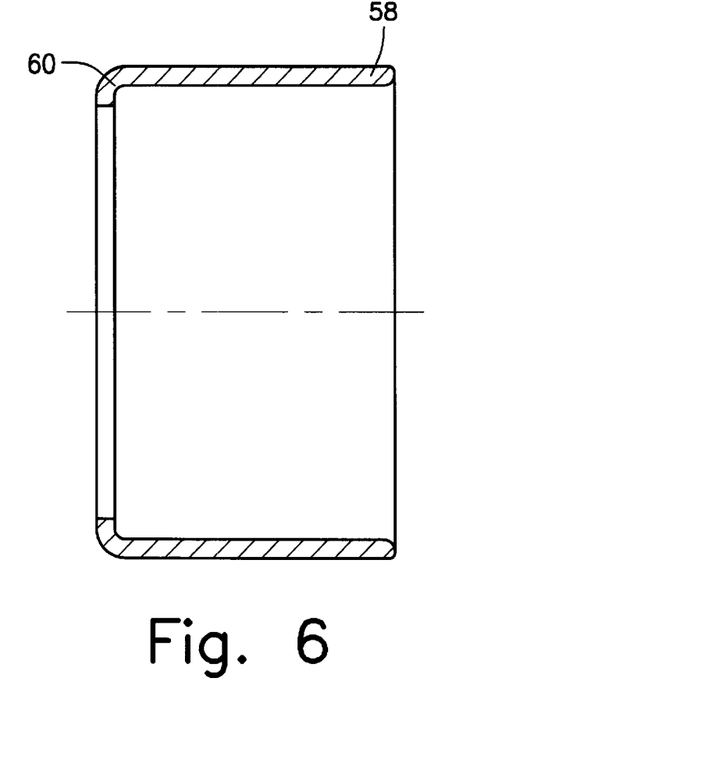
FIG. 6 shows a longitudinal section of a caulking sleeve.

This sealing seat is secured by a sleeve 58, depicted in detail in FIG. 6, which virtually surrounds sealing segment 48. Sleeve 58 has a neck-shaped shoulder 60, molded to the inside, which functions, on the one hand, as supporting element for segment 32, and, on the other hand, as a limit stop for attachment segment 48. Sleeve 58 is plastically deformed by the application of an external mechanical force, at least in areas, a so-called caulking, so that attachment segment 48 is fixedly squeezed between sleeve 58 and segment 32. Overall, the result is thus a mechanically more secure connection, i.e., one capable of sustaining strain between pipe element 50 and protective sleeve 24, or housing 16, and the connection also having, in addition, great sealing effectiveness.

Figures 4, 5:
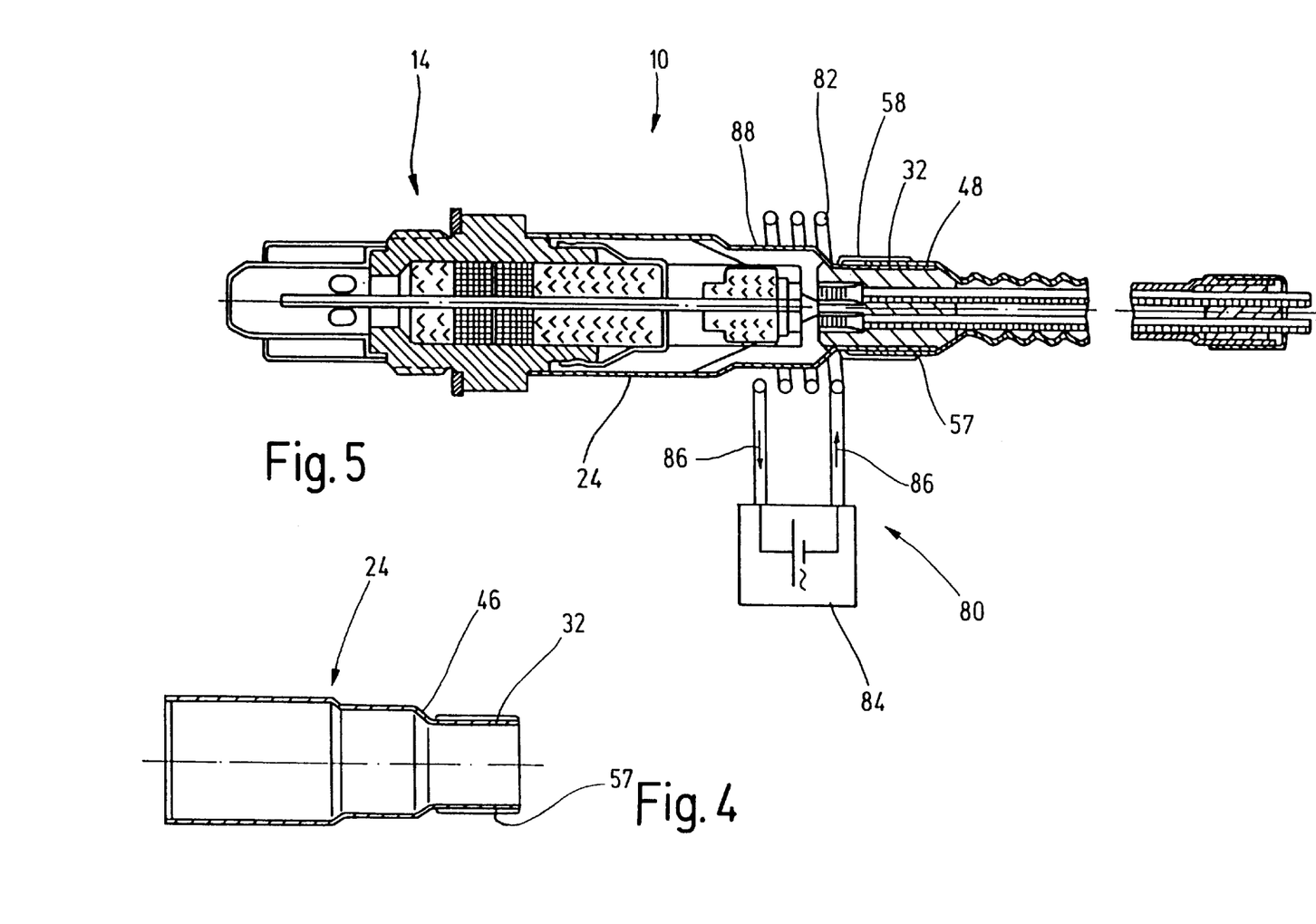
FIG. 4 shows another longitudinal section of the protective sleeve.
FIG. 5 schematically shows a manufacturing process of a sealing seat.

As shown in FIG. 4, segment 32 of protective sleeve 24 has a coating 57 on its outer periphery. According to a first exemplary embodiment, coating 57 is made of a PTFE material, which is applied to segment 32 using an appropriate method. For this purpose, special coating techniques are known which permit metals to bond, e.g., to protective sleeve 24 and PTFE material 32. Coating 57 is applied at relatively low strength, so that it is possible to slide mounting end 48 onto segment 32 having its coating 57.

As a result of providing for coating 57 of a PTFE material in the area of hollow element 50, which is slid onto protective sleeve 24, a sealing seat 61 is formed between coating 57, which is permanently bonded to protective sleeve 24, and attachment segment 48 of hollow element 50. The sealing surfaces are constituted, on the one hand, by the outer surface of coating 57 and, on the other hand, by the inner shell of attachment segment 48. In this way, a relatively large sealing surface is achieved, which prevents contamination from penetrating into protective sleeve 24 and thus into housing 16. Since both coating 57 and hollow element 50 are made of a PTFE material, sealing seat 61 is formed out of two sealing surfaces of PTFE material, which are situated directly opposite each other. PTFE material is known to have distinctly hydrophobic properties, i.e., mutually facing boundary layers of PTFE material achieve a force-locking fit. At the same time, a water-repellant effect is thus achieved, so that even mist-like contaminants, or moisture, are not able to pass through sealing seat 61.

According to a further exemplary embodiment, coating 57 can also be made of a PFA material. It is known that PFA materials begin to liquefy when heated to a certain temperature, approximately from 310 to 330° C. In this temperature range, a certain viscosity of the PFA material is achieved, so that it develops an adhesive effect. These known properties of PFA material are exploited by heating sealing seat 61 to a defined temperature, after sliding attachment segment 48 onto protective sleeve 24 having coating 57.

For this purpose, the device indicated schematically in FIG. 5 can be used. FIG. 5 shows, on the one hand, the longitudinal section of measuring device 10 as shown in FIG. 1, so that generally the description in that regard can be referred to.

For manufacturing a form- and force-locking sealing seat 61 between attachment segment 48 and coating 57, and thus protective sleeve 24, provision is made for a device, designated throughout as 80. Device 80 possesses an induction coil 82, whose inner diameter is selected such that measuring instrument 10, at least with respect to segment 32 of protective sleeve 24, can be inserted into it. Induction coil 82 is connected to a voltage source, for example, a high frequency generator 84. Moreover, the coil lines of induction coil 82 can be designed as hollow leads so that a circulation circuit 86 of a coolant, for example, air or water, can be maintained. The manner of functioning of a such a device 80 operating on the basis of an induction coil 82, is well known. By switching on high frequency generator 84, heat energy is produced by induction coil 82, the heat energy making it possible to apply this heat energy in a defined manner to measuring device 10. Since protective sleeve 24 is made of a metallic material, it is suitable as a heat conductor. By heating protective sleeve 24 at its segment 88, heat is conducted, among other things, in the direction of segment 32, so that coating 57 made of PFA material applied to segment 32 is also heated. Through the defined heating, which can be adjusted, for example, regarding a period of heating, a level of current flow through induction coil 82, or other suitable precautions, coating 57 is heated to a defined degree so that it becomes viscous.

As a result of the subsequent caulking of sleeve 58, attachment segment 48 is pressed against coating 57, which has melted from the effect of the heat, so that, after the cooling and resolidifying of coating 57, an interior form and force locking bond results between attachment segment 48 and coating 57. In this way, sealing seat 61 is formed having permanent, powerful sealing effectiveness.

Whether coating 57 is manufactured out of a PTFE material or a PFA material, it is assured that, due to operating temperatures of, for example, about 250 to 300° C., which arise during the normal use of measuring device 10, a temperature resistance of sealing seat 61 is produced such that measuring device 10 is permanently sealed off against penetration of external contaminants.

Shell 62 (shown in FIG. 2) of guide segment 54 of hollow element 50 has a structured surface 64. Structured surface 64 is created as a result of shell 62 having segments of varying, and optionally repeating, diameters across the axial extent of guide segment 54. Structured surface 64 can be designed such that a spiral-shaped pattern results. According to further exemplary embodiments, shell 62 can have rings which are concentrically spaced with regard to each other. A diameter of the rings, in this context, can vary across the axial length of guide segment 54, i.e., the latter becomes smaller or larger, starting from, for example, attachment segments 48 and/or 52. A further embodiment provides that structured surface 64 has the shape of an external thread. In this context, the resulting thread-shaped structured surface 64 can for its part have varying thread pitches across the axial extent of guide segment 54.

Figures 2, 2A, 2B:
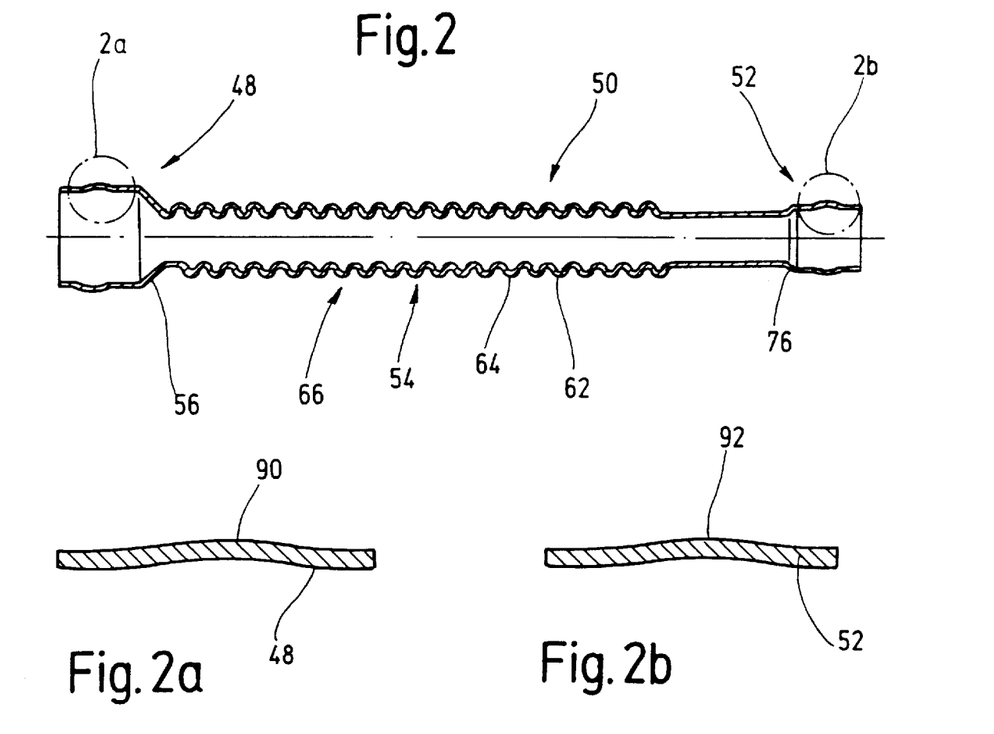
FIG. 2 shows a longitudinal section of an elastic hollow element.
FIG. 2a shows a detailed illustration of a first attachment segment of the elastic hollow element.
FIG. 2b shows a detailed illustration of a second attachment segment of the elastic hollow element.

As a result of the shape of structured surface 64, which, as explained, can be of the most varying kinds, hollow element 50 is mechanically stabilized, while nevertheless generally remaining flexible due to its elastic material. Since hollow element 50 accommodates connecting wires 20, the former constitutes a kind of protective device 66 for connecting wires 20. With the retained elasticity of hollow element 50, necessary for supporting connecting wires 20 at their mounting location, at the same time, as a result of structured surface 64, protection against bending is achieved, which prevents elastic hollow element 50 and thus connecting lines 20, supported therein, from being bent sharply. Although, as explained, a sharp-edged bending is impossible, in the event of a bending of hollow element 50, additional support is achieved as a result of conical segment 56 between attachment segment 48 and guide segment 54, in that the conical segment contacts conical shell 40 of support sleeve 30.

Since elastic hollow element 50 is made of a PTFE material, in addition to the mechanical protection of connecting lines 20, there is also protection against an impermissible heating of connecting lines 20. PTFE material, as is well known, has a high resistance to heat, which, in any case, in the range of temperatures expected at the mounting location of measuring device 10 of, for example, approximately 250 to 300° C., permits a lasting protected support of connecting lines 20 and assures a durable seal for measuring device 10 against the entry of external contaminants.

Figure 8:
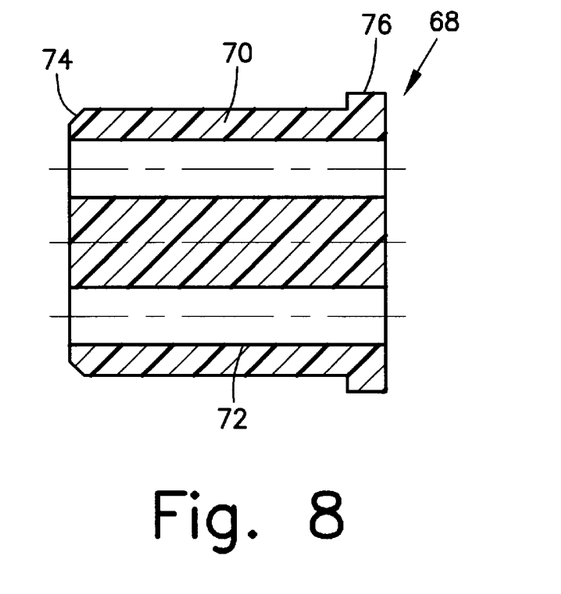
FIG. 8 shows a longitudinal section and a t op view of another support sleeve.
Figure 8A:
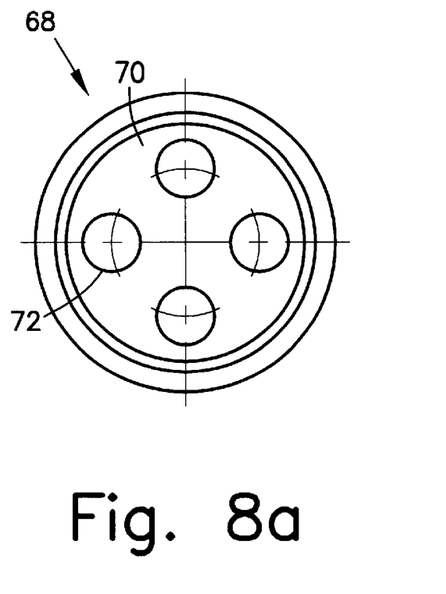
FIG. 8a shows a top view of the support sleeve illustrated in FIG. 8.
Figure 9:
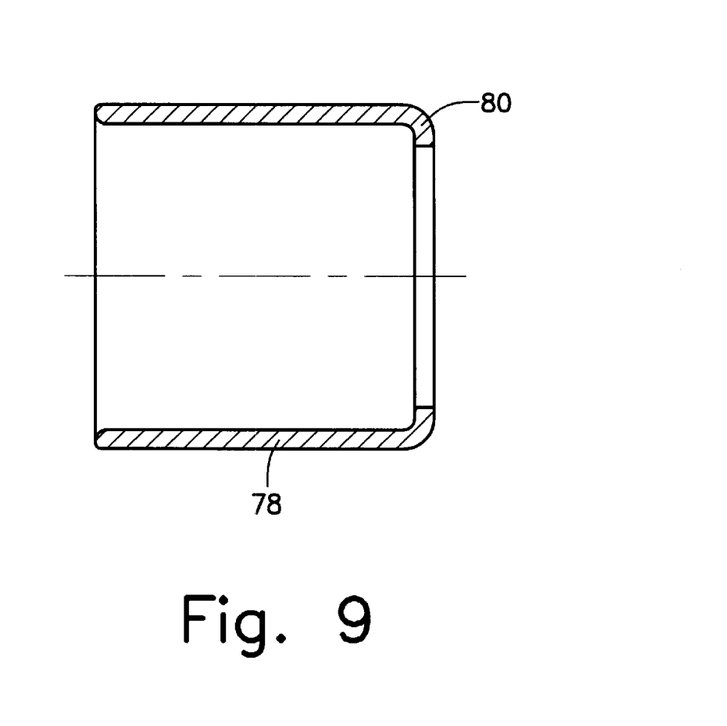
FIG. 9 shows a longitudinal section of a further caulking sleeve.

Attachment segment 52, away from the gas to be measured, accommodates a further support sleeve 68. Like support sleeve 30, support sleeve 68, which is shown in greater detail in FIG. 8, is inserted into attachment segment 52. Support sleeve 68 has a substructure 70, which has through holes 20 corresponding to the number of connecting lines 20. At its one end, in the axial direction, substructure 70 has a conical taper 74 and, at its other end, has a collar 76. Based on the assembled state of entire measuring device 10, shown in FIG. 1, it is clear that taper 74 is supported on a conical segment 76 of hollow element 50, which is situated between attachment segment 52 and guide segment 54. Collar 76 acts as a limit stop for attachment segment 52, which is slid onto support sleeve 70. Attachment segment 52, and thus support sleeve 68, is embraced by a sleeve 78. As FIG. 9 shows in greater detail, sleeve 78 has a collar-shaped shoulder 80, aligned radially toward the inside, which acts as a limit stop for collar 76 of support sleeve 70. Support sleeve 78 after being slid into place, is also plastically deformed, at least in areas, so that attachment segment 52 between support sleeve 70 and sleeve 78 is virtually squeezed together and is thus locked in position. On the basis of the relatively large contact surface between attachment segment 58 and sleeve 78, or support sleeve 70, a large sealing surface results, preventing impurities or contaminants from entering into hollow element 50. Connecting lines 20 are guided via through holes 72 of support sleeve 70, sealed guidance being assured here as with support sleeve 30. Outside of support sleeve 70, connecting lines 20 either can have a contact device, undepicted here, for connecting to further connecting lines leading to an evaluation circuit, or connecting lines 20 are directly led to this circuit.

Support sleeve 68 is made of an elastic material, for example, silicon rubber, so that the sleeve, under light pressure, can be pressed into attachment segment 52. In this way, the sealing action is assured both between support sleeve 70 and attachment segment 52 as well as between support sleeve 70 and connecting lines 20 guided through through holes 72. If attachment segment 52 is arranged in an installation area which is subject to relatively high temperature stresses, then support sleeve 70 can likewise be made of a PTFE material. In this case, support sleeve 70 can be glued in place, for example, in attachment segment 52, which is also, like the entire hollow element, made of a PTFE material, in that this area is heated for a short time to above the melting temperature of the PTFE material, so that a fusion between support sleeve 70 and attachment segment 52 takes place.

Attachment segments 48 and 52, as shown in FIGS. 2a and 2b, have, in each case, a nub-like protuberance 90 and 92 respectively. The nub-like protuberances 90 and 92 act to fix sleeves 58 and 78, respectively, during assembly. For the sealing action, or the mechanical protection of hollow element 50 against bending, protuberances 82 and 84 have no functional significance.

What is claimed is:

1. A measuring device, comprising:
    electrical connecting lines;
    a sensor element arranged at a predetermined measuring point and coupled to at least one of the electrical connecting lines;
    a housing enclosing the sensor element;
    a protective sleeve;
    a protective device enclosing and routing the electrical connecting lines, the protective device including an elastic hollow element having an attachment segment and a guide segment, the attachment segment surrounding a portion of the protective sleeve; and
    a securing sleeve to secure the attachment segment;
    wherein the attachment segment is connected to the protective sleeve via the securing sleeve with a force-locking fit and a form-locking fit to form a sealing seat.

2. The measuring device according to claim 1, wherein the measuring device is an electrochemical sensor.

3. The measuring device according to claim 1,
    wherein the attachment segment engages with fitting piece of the attachment segment engages with a fitting piece of the sensor element.

4. The measuring device according to claim 1, wherein the elastic hollow element includes a shell having a structured undulating design, the structured undulating design of the shell extending over the guide segment.

5. The measuring device according to claim 4, wherein the structured undulating design is formed from sections having varying diameters.

6. The measuring device according to claim 5, wherein the sections are repeated over an axial extent of the guide segment.

7. The measuring device according to claim 4, wherein the structured undulating design has a spiral shape.

8. The measuring device according to claim 4, wherein the structured undulating design is composed of concentric rings, each of the concentric rings being situated at a defined distance from another one of the concentric rings.

9. The measuring device according to claim 8, wherein the structured undulating design has a shape of an external thread.

10. The measuring device according to claim 9, wherein the external thread has varying pitches over an axial extent of the guide segment.

11. The measuring device according to claim 4, wherein the structured undulating design has a shape of an external thread.

12. The measuring device according to claim 4, wherein the attachment segment is arranged on one side of the guide segment.

13. The measuring device according to claim 12, wherein the attachment segment accommodates a support sleeve having through holes for guiding the electrical connecting lines.

14. The measuring device according to claim 13, wherein the serving sleeve is at least partially plastically deformed.

15. The measuring device according to claim 14, wherein the serving sleeve contacts the attachment segment over a large surface area, and the attachment segment contacts the support sleeve to form a large sealing surface.

16. The measuring device according to claim 13, wherein the protective sleeve at least partially encloses the support sleeves.

17. The measuring device according to claim 16, wherein the protective sleeve segment has a coating in an area of the sealing seat.

18. The measuring device according to claim 17, wherein the coating is a polytetrafluoroethylene coating.

19. The measuring device according to claim 17, wherein the coating is a polyfluoroamide coating.

20. The measuring device according to claim 17, wherein the coating is heated to a temperature above a melting point of the coating, and an outer surface of the measuring device in the area of the sealing seat is deformed via a mechanical force one of after the heating and at the same time as the heating to provide the form-locking fit and the force-locking fit.

21. The measuring device according to claim 20, wherein the coating is inductively heated.

22. The measuring device according to claim 13, wherein the support sleeve has a conical shell surface for supporting a transition area on the elastic hollow element which is between the attachment segment and the guide segment, the transition area having a conical surface matching the conical shell surface.

23. The measuring device according to claim 1, wherein the protective device is composed of a polytetraflouroethylene material.

* * * * *

UNITED STATES PATENT AND TRADEMARK OFFICE
CERTIFICATE OF CORRECTION

PATENT NO. : 6,342,140 B1
DATED : January 29, 2002
INVENTOR(S) : Helmut Weyl et al.

It is certified that error appears in the above-identified patent and that said Letters Patent is hereby corrected as shown below:

Title page,
Item [73], change "Stuggart to -- Stuttgart --.

Column 1,
Line 31, delete "DG".
Line 56, change "invention," to -- invention --.

Column 2,
Line 63, change "oven" to -- given --.

Column 8,
Line 58, change "sleeves." to -- sleeve. --.

Signed and Sealed this

Twenty-fifth Day of March, 2003

JAMES E. ROGAN
*Director of the United States Patent and Trademark Office*